US011266590B2

(12) United States Patent
Zhang et al.

(10) Patent No.: US 11,266,590 B2
(45) Date of Patent: Mar. 8, 2022

(54) SKIN CARE COMPOSITION (71) Applicant: The Procter & Gamble Company, Cincinnati, OH (US)

(72) Inventors: Lu Zhang, Singapore (SG); Namrata Manohar Bhandarkar, San Francisco, CA (US); Paul Robert Tanner, Cincinnati, OH (US); Shawn David McConaughy, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/548,292

(22) Filed: Aug. 22, 2019

(65) Prior Publication Data

US 2020/0060961 A1 Feb. 27, 2020

Related U.S. Application Data (60) Provisional application No. 62/721,613, filed on Aug. 23, 2018.

(51) Int. Cl.
| | | |
|---|---|---|
| *A61Q 17/04* | (2006.01) |
| *A61K 8/81* | (2006.01) |
| *A61K 8/89* | (2006.01) |
| *A61K 8/49* | (2006.01) |
| *A61K 8/26* | (2006.01) |
| *A61K 8/06* | (2006.01) |
| *A61K 8/25* | (2006.01) |
| *A61K 8/73* | (2006.01) |

(52) U.S. Cl.
CPC ............... *A61K 8/89* (2013.01); *A61K 8/06* (2013.01); *A61K 8/25* (2013.01); *A61K 8/26* (2013.01); *A61K 8/4946* (2013.01); *A61K 8/732* (2013.01); *A61K 8/8147* (2013.01); *A61Q 17/04* (2013.01)

(58) Field of Classification Search
CPC ... A61K 8/89; A61K 8/06; A61K 8/25; A61K 8/26; A61K 8/4946; A61K 8/732; A61K 8/8147; A61Q 17/04
See application file for complete search history.

(56) References Cited

U.S. PATENT DOCUMENTS

| | | | | |
|---|---|---|---|---|
| 5,041,281 A * | 8/1991 | Strobridge | ............... | A61K 8/06 424/59 |
| 5,585,104 A * | 12/1996 | Ha | ........................... | A61K 8/06 424/401 |
| 8,778,365 B1 * | 7/2014 | Hardas | ................... | A61K 47/38 424/400 |
| 2002/0161104 A1 | 10/2002 | Labrousse | | |
| 2010/0183531 A1 | 7/2010 | Johncock | | |
| 2011/0014139 A1 | 1/2011 | Viala | | |
| 2013/0330385 A1 | 12/2013 | Maass | | |
| 2014/0370062 A1 | 12/2014 | Fageon | | |
| 2015/0174046 A1 | 6/2015 | Galdi | | |
| 2015/0209259 A1 | 7/2015 | Schade | | |
| 2015/0216766 A1 * | 8/2015 | Tanaka | ..................... | A61K 8/89 424/401 |
| 2016/0030313 A1 * | 2/2016 | Jansen | ................... | A61K 8/732 424/60 |
| 2016/0367448 A1 | 12/2016 | Youssef | | |
| 2016/0374933 A1 | 12/2016 | Tanner | | |
| 2017/0312190 A1 * | 11/2017 | Gonazales | ........... | A61K 8/8117 |
| 2018/0228717 A1 | 8/2018 | Kubota | | |
| 2018/0280282 A1 * | 10/2018 | McConaughy | ...... | A61Q 19/007 |

FOREIGN PATENT DOCUMENTS

| | | |
|---|---|---|
| CN | 104758220 A | 7/2015 |
| DE | 19923667 A1 | 11/2000 |
| DE | 19923670 A1 | 11/2000 |
| DE | 19923671 A1 | 11/2000 |
| DE | 19923672 A1 | 11/2000 |
| DE | 19923712 A1 | 11/2000 |
| DE | 19923715 A1 | 11/2000 |
| DE | 19923773 A1 | 11/2000 |
| DE | 19942714 A1 | 3/2001 |
| DE | 10037558 A1 | 2/2002 |
| DE | 102007028497 A1 | 12/2008 |
| DE | 102009048556 A1 | 4/2011 |
| DE | 102009048557 A1 | 4/2011 |
| DE | 102009048558 A1 | 4/2011 |
| DE | 102010063894 A1 | 6/2012 |
| DE | 102012211790 A1 | 1/2014 |
| DE | 102013213170 A1 | 1/2015 |
| DE | 102013213174 A1 | 1/2015 |
| DE | 102014206219 A1 | 10/2015 |
| DE | 102014206221 A1 | 10/2015 |
| DE | 102014206224 A1 | 10/2015 |
| EP | 0761202 A3 | 6/1999 |
| EP | 1077062 A2 | 2/2001 |
| EP | 1213010 A2 | 6/2002 |
| EP | 1310236 A1 | 5/2003 |
| EP | 1310239 A1 | 5/2003 |
| EP | 1728501 A1 | 12/2006 |
| EP | 1837007 A2 | 7/2008 |
| EP | 3093004 A1 | 11/2016 |
| EP | 3093005 A1 | 11/2016 |
| EP | 3093006 A1 | 11/2016 |
| EP | 3093007 A1 | 11/2016 |
| EP | 3093008 A1 | 11/2016 |
| EP | 3093009 A1 | 11/2016 |
| JP | 5502338 B2 | 3/2014 |
| KR | 101821934 B1 | 1/2018 |
| WO | WO03/015727 A1 | 2/2003 |
| WO | WO2006034992 A1 | 4/2006 |
| WO | WO2006035000 | 4/2006 |
| WO | WO2008/018644 A1 | 2/2008 |
| WO | WO2008119448 A1 | 10/2008 |
| WO | WO2012139246 A2 | 10/2012 |
| WO | WO2015188335 A1 | 12/2015 |
| WO | WO2016166345 A1 | 10/2016 |

OTHER PUBLICATIONS

International Search Report and Written Opinion of the International Searching Authority, PCT/US2019/047611, dated Nov. 25, 2019, 14 pages.

\* cited by examiner

*Primary Examiner* — Celeste A Roney
(74) *Attorney, Agent, or Firm* — Alexandra S. Anoff; John G. Powell (57) ABSTRACT

The present disclosure generally relates to a skin care composition for providing ultraviolet (UV) protection to skin with desired sensory feels by the consumers. More specifically, the present disclosure relates to a UV-blocking skin care composition having both proper stringiness and proper viscosity.

18 Claims, 1 Drawing Sheet

SKIN CARE COMPOSITION

FIELD OF THE INVENTION

The present disclosure generally relates to a skin care composition for providing ultraviolet (UV) protection to consumers with desired skin feels. More specifically, the present disclosure relates to a UV-blocking composition having a balance between stringiness and viscosity.

BACKGROUND OF THE INVENTION

It is well known that UV radiation (that is, wavelengths ranging from 280 nm to 400 nm) can cause damages to the human epidermis. More particularly, UV rays with wavelengths ranging from 320 to 400 nm (known as UV-A) may cause hyperpigmentation of the skin and long-term damages therein (such as wrinkles and fine lines), and rays with wavelength ranging from 280 to 320 nm (known as UV-B) can lead to erythemas and skin burns. In order to prevent or minimize damages or harmful effects caused by UV radiation, skin care compositions containing UV-blocking compounds in varying concentrations (also called sunscreen compositions) are provided.

In that sunscreen compositions are more frequently used during warmer seasons, such as in the summer, consumers desire a fresh, water-like feels to the skin upon use of sunscreen compositions. Such desire is particularly strong for consumers who use sunscreen compositions on a daily basis. However, most sunscreen compositions on the market are oil-based, so it is generally difficult to provide such fresh, water-like feels to the skin. Rather, such oil-based sunscreen compositions tend to impart a greasy feel to the skin. Such negative skin feels may be particularly worse for high-SPF UV-blocking products, because such products contain significantly increased level of UV-blocking actives. Particularly, high SPF UV-blocking compositions, while being spread on the skin, would result in a very sticky, oily and greasy skin feel. It is quite unpleasant for consumers to leave a greasy mark on everything they touch after applying sunscreens. Accordingly, consumers expect UV-blocking compositions having both a high SPF index and a good skin feel (for example, good spreadability, non-greasy, non-sticky/tacky, non-oily/shiny, refreshing, and the like).

In order to meet such consumer expectation, a number of sunscreen products have been developed to provide improved sensory benefits. Unfortunately, few products can meet all consumers' needs. For example, some products have low viscosity to provide good spreadability but are highly tacky, while some other products are not quite tacky but are hard to spread. It is difficult to formulate a UV-blocking composition that provides consumers with both a high SPF index and a good skin feel.

Hence, there is a need for a UV-blocking composition which provides not only effective UV protection, but also fresh, non-greasy feel to the skin. It is also advantageous to provide a sunscreen composition which is easy to apply and not messy upon use. It is also advantageous to provide a sunscreen composition which can be suitably used as a foundation base product.

More particularly, it is highly advantageous to develop a UV-blocking composition providing consumers with a balanced feel between spreadability and tackiness.

SUMMARY OF THE INVENTION

A novel technology for formulating a UV composition is developed by the inventors to meet the needs as mentioned above. Particularly, it was surprisingly discovered that a high SPF skin care composition exhibiting a Mean Break Time within a specific range (such as between about 0.01 s and about 0.7 s as measured by the Tack Method described hereinafter) and a dynamic viscosity within a specific range (such as between about 0.01 Pa·S and about 0.70 Pa·S as measured by the Rheology Method described hereinafter at 100 s$^{-1}$) provides consumers with a desirable skin feel. Particularly, such high SPF skin care composition might strike a good balance between different sensory aspects, such as spreadability, oiliness, stickiness/stringiness, water-light feel, refreshing feel, and/or shine.

Furthermore, it was surprisingly discovered that high SPF skin care compositions comprising a low-viscosity dimethicone, a particulate material and a water-soluble UV-blocking active can meet the above described consumers' needs, that is, to provide effective UV protection, while leaving a fresh, non-greasy feel to the skin, and yet being easy to apply and/or not messy upon use. More particularly, the compositions of the present disclosure may provide consumers with balanced feels that resembles the sensory perception left behind after applying water to the skin, without any heavy or greasy feel.

In one aspect, the present disclosure is directed to a skin care composition that may comprise:
a) from about 7% to about 90%, by weight of the composition, of one or more UV-blocking actives;
b) from about 2% to about 90%, by weight of the composition, of a dimethicone having a kinematic viscosity of from 0.1 cSt to 2000 cSt as measured by the Rheology Method described hereinafter; and
c) from about 3% to about 90%, by weight of the composition, of a particulate material.

In another aspect, the present disclosure is directed to a skin care composition comprising from 15% to 55% of one or more UV-blocking actives by weight of the composition, wherein the composition may exhibit: (1) a Mean Break Time of between about 0.01 s and about 0.7 s as measured by the Tack Method, and (2) a dynamic viscosity of between about 0.01 Pa·S and about 0.70 Pa·S as measured by the Rheology Method at 100 s$^{-1}$.

DETAILED DESCRIPTION OF THE INVENTION

As used in the description and the appended claims, the singular forms "a," "an," and "the" are intended to include the plural forms as well, unless the context clearly indicates otherwise. All percentages and ratios used herein are by weight of the total composition, unless otherwise designated. The number of significant digits conveys neither a limitation on the indicated amounts nor on the accuracy of the measurements. All numerical amounts are understood to be modified by the word "about" unless otherwise specifically indicated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

Definitions

"Apply" or "application," as used in reference to a composition, means to apply or spread the composition onto keratinous tissue such as the epidermis.

"Keratinous tissue" refers to keratin-containing layers disposed as the outermost protective covering of mammals (e.g., humans, dogs, cats, etc.) which includes, but is not limited to, skin, lips, hair, toenails, fingernails, cuticles, hooves, etc.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"UV-blocking active" means a material recognized by a skilled artisan in the field of sunscreen formulation to be a dermatologically acceptable UV-absorbing or UV-reflecting active material. Such UV-blocking actives may be described as being UVA-blocking and/or UVB-blocking active agents. Approval by a regulatory agency is generally required for inclusion of active agents in formulations intended for human use. Those active agents which have been or are currently (per 21 C.F.R. part 352) approved by the U.S. Food and Drug Administration as acceptable for use in over-the-counter sunscreen drug products include organic and inorganic substances including, without limitation, para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the U.S., but are approved for over-the-counter use in other regions or countries such as Europe (per European Commission's Cosmetic Directive Regulation), Japan, China, Australia, New Zealand, or Canada include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved materials is currently expanding, those of ordinary skill will recognize that the invention is not limited to UV-blocking actives currently approved for human use but are readily applicable to those that may be allowed in the future.

"Skin care composition" refers to topical personal care compositions for regulating and/or improving a skin condition. Some nonlimiting examples of skin care compositions include solutions, aerosols, liposomes, creams, moisturizers, gels, lotions, ointments, serums, sticks, spray, emulsions, or any other dispersions, for example facial cleansers, body washes, a sunscreen cream, a sunscreen spray, a sunscreen emulsion, a skincare base, a makeup base, a tinted cream, a foundation in liquid, an eye contour care product, a concealing care serum, a concealer stick or a natural makeup product for the lips, a liquid gloss, a lipstick paste, and the like.

"Topical" refers to a composition that is intended to be applied to a keratinous surface such as skin or hair.

"Derivatives" means an ester, ether, amide, hydroxy, and/or salt structural analogue of the relevant compound.

Skin Care Composition

The skin care compositions herein are configured for topical application to keratinous tissue. Particularly, the skin care compositions may include dimethicone and a particulate material as well as a water-soluble UV-blocking active at specific amounts, and such compositions may provide the desired feels including non-greasy, non-sticky (indicated by Mean Break Time), non-shiny, refreshing and easy to spread (indicated by dynamic viscosity). More particularly, the skin care compositions are UV-blocking compositions or sunscreen compositions.

Without being limited by theory, it is believed that the stringiness and viscosity of a skin care composition are critical for providing the desired feel on the skin. Stringiness as used herein is characterized by a Mean Break Time, i.e., the time it takes for strands of the composition to break when an object in contact with the composition is moved away from the composition (i.e., how long a force must be applied to break contact). Stringiness are determined according to the Tack Method described in the Test Methods section below.

The dynamic viscosity of a fluid expresses its resistance to shearing flows, where adjacent layers move parallel to each other with different speeds. Without being limited by theory, it is believed that dynamic viscosity indicates the spreadability of a skin care composition. Dynamic viscosity herein is determined according to the Rheology Method described in the Test Methods section below.

In some embodiments, the skin care composition of the present invention may exhibit a Mean Break Time of between about 0.01 s and about 0.7 s, preferably between about 0.05 s and about 0.4 s, more preferably between 0.08 s and about 0.3 s, and most preferably between about 0.10 s and about 0.25 s, for example about 0.11 s, about 0.12 s, about 0.13 s, about 0.14 s, about 0.15 s, about 0.16 s, about 0.17 s, about 0.18 s, about 0.19 s, about 0.20 s, about 0.21 s, about 0.22 s, about 0.23 s, about 0.24 s, about 0.25 s or any ranges therebetween, as measured by the Tack Method. Additionally or alternatively, the composition may exhibit a dynamic viscosity of between about 0.01 Pa·S and about 0.70 Pa·S, preferably between about 0.20 Pa·S and about 0.70 Pa·5, more preferably between about 0.35 Pa·S and about 0.70 Pa·S, and most preferably between about 0.40 Pa·S and about 0.68 Pa·S, for example about 0.40 Pa·S, about 0.42 Pa·S, about 0.44 Pa·S, about 0.46 Pa·S, about 0.48 Pa·S, about 0.50 Pa·S, about 0.52 Pa·S, about 0.54 Pa·S, about 0.56 Pa·S, about 0.58 Pa·S, about 0.60 Pa·S, about 0.62 Pa·S, about 0.64 Pa·S, about 0.66 Pa·S or any ranges therebetween, as measured by the Rheology Method at 100 $s^{-1}$. Preferably, the skin care composition of the present invention exhibits both a Mean Break Time and a dynamic viscosity within the above-described ranges.

In preferred embodiments, the composition exhibits a Mean Break Time of between about 0.10 s and about 0.25 s, as measured by the Tack Method, and/or a dynamic viscosity of between about 0.40 Pa·S and about 0.68 Pa·S, as measured by the Rheology Method at 100 $s^{-1}$.

In more preferred embodiments, the composition exhibits a Mean Break Time of between about 0.18 s and about 0.25 s, as measured by the Tack Method, and/or a dynamic viscosity of between about 0.48 Pa·S and about 0.66 Pa·S, as measured by the Rheology Method at 100 $s^{-1}$.

UV-Blocking Actives

The compositions of the present disclosure may comprise a UV-blocking active. As used herein, the term of "UV-blocking active" includes both sunscreen agents and physical sunblocks. Suitable UV-blocking actives may be organic or inorganic. Suitable UV-blocking actives are well known. The composition may comprise an amount of UV-blocking active prescribed or proposed by regulatory agencies in the US, Europe, Japan, China, Australia, New Zealand, or Canada. In particular embodiments, the composition comprises from about 0.5%, 1%, 2%, or 3% to about 50%, 40%, 30%, or 20%, by weight of the composition, UV-blocking active. In some embodiments, the composition may comprise a sufficient amount of UV-blocking active to yield a Sun Protection Factor (SPF) of at least about 15, 30 45, 50 or 50+. SPF testing is conventional and well understood in the art. A suitable SPF test is prescribed in ISO24444.

In some embodiments, the composition may comprise from about 10% to about 60%, preferably from about 15% to about 55%, more preferably from about 17% to about 50%, and most preferably from about 20% to about 45%, by weight of the composition, of one or more UV-blocking actives.

Suitable UV-blocking actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, diisopropyldibenzoylmethane, 4,4'-dimethoxy dibenzoylmethane, 4-tert-butyl-4'-methoxy dibenzoylmethane (i.e., butyl methoxydibenzoylmethane or avobenzone)(commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Other suitable UV-blocking actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl salicylate, homomenthyl salicylate (homosalate), glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures of these compounds.

Other suitable UV-blocking actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), ethylhexyl triazone (commercially available as Uvinul® T 150 from BASF), drometrizole trisiloxane (marketed as Mexoryl XL by L'Oreal), sodium dihydroxy dimethoxy disulfobenzophenone (i.e., benzophenone-9, commercially available as Uvinul® DS 49 from BASF), diethylamino hydroxybenzoyl hexyl benzoate (commercially available as Uvinul® A Plus from BASF), diethylhexyl butamido triazone (i.e., Iscotrizinol, commercially available as Uvasorb® HEB by 3V Sigma), polysilicone-15 (i.e., commercially available as PARSOL® SLX from DSM), isoamyl p-methoxycinnamate (i.e., amiloxate, commercially available as Neo Heliopan® E 1000 from Symrise), and mixtures thereof.

In some embodiments, the UV-blocking active in the composition of the present disclosure may comprise a water-soluble UV-blocking active and optionally, an additional UV-blocking active. Preferably, the water-soluble UV-blocking active is selected from the group consisting of phenylbenzimidazole sulfonic acid, terephthalylidene dicamphor sulfonic acid, disodium phenyl dibenzimidazole tetrasulfonate and any combinations thereof, and/or the additional UV-blocking active is selected from the group consisting of homosalate (homomethyl salicylate), octocrylene, ethylhexyl triazone, butyl methoxydibenzoylmethane, ethylhexyl salicylate, ethylhexyl methoxycinnamate, oxybenzone, octyltriazone, diethylamino hydroxybenzoyl hexyl benzoate, zinc oxide, titanium dioxide, bis-ethylhexyloxyphenol methoxyphenyl triazine, triethanolamine salicylate, methylene bis-benzotriazolyl tetramethylbutylphenol and any combinations thereof. More preferably, the water-soluble UV-blocking active is phenylbenzimidazole sulfonic acid, and/or the additional UV-blocking active is selected from the group consisting of homosalate (homomethyl salicylate), octocrylene, butyl methoxydibenzoylmethane, diethylamino hydroxybenzoyl hexyl benzoate, bis-ethyl-hexyloxyphenol methoxyphenyl triazine, ethylhexyl methoxycinnamate and any combinations thereof.

Particularly, the composition may comprise from about 0.01% to about 50%, more preferably from about 0.1% to about 30%, yet more preferably from about 0.5% to about 10%, and most preferably from about 1% to about 5%, for example about 1%, about 1.5%, about 2%, about 2.5%, about 3%, about 3.5%, about 4%, about 4.5%, about 5% or any ranges therebetween, by weight of the composition, of the water-soluble UV-blocking active, and/or the composition may comprise from about 0.01% to about 50%, more preferably from about 0.1% to about 45%, yet more preferably from about 1% to about 40%, yet more preferably from about 5% to about 35%, and most preferably from about 13% to about 21%, for example about 13%, about 14%, about 15%, about 16%, about 17%, about 18%, about 19%, about 20%, about 21% or any ranges therebetween, by weight of the composition, of the additional UV-blocking active. Without intending to be bound by theory, it is believed that the combined use of a preferred concentration of the water-soluble UV-blocking active and a preferred concentration of the additional UV-blocking active at some specific ratios brings about additional benefits, such as even better sensory benefits.

Preferably, in some embodiments, the composition of the present disclosure is essentially free of physical sunblocks, such as metal oxide (e.g., zinc oxide or titanium oxide).

Without intending to be bound by theory, it is believed that the absence of physical sunblocks is useful to prevent uncomfortable skin feel.

Preferably, in some embodiments, in the composition of the present disclosure, the concentration of homosalate is from 6% to 10% by weight of the composition, the concentration of octocrylene is from 7% to 11% by weight of the composition, and the concentration of butyl methoxydibenzoylmethane is from 1% to 5% by weight of the composition.

The UV-blocking actives of the present invention may be encapsulated. Examples of commercially available encapsulated sunscreen actives include, but are not limited to: Eusolex UV-Pearls 2292 (Merck/EMD Chemicals), which includes water, ethylhexyl methoxycinnamate, silica, phenoxyethanol, PVP, chlorphenesin, disodium EDTA, and BHT; Silasoma ME (Seiwa Kasei Co., Ltd), which includes water, polysilicone-14, and ethylhexyl methoxycinnamate; Silasoma MEA (Seiwa Kasei Co., Ltd), which includes water, polysilicone-14, ethylhexyl methoxycinnamate, and butyl methoxydibenzoylmethane; Silasoma MEP(S) (Seiwa Kasei Co., Ltd), which includes water, ethylhexyl methoxycinnamate, diethylamino hydroxybenzoyl hexyl benzoate, and polysilicone-14; Suncaps 664 (Particle Sciences, Inc.), which includes, ethylhexyl methoxycinnamate, synthetic beeswax, PEG-20, copernicia cerifera (carnauba) wax, Bis-PEG-12 dimethicone, beeswax, VP/Eicosene copolymer, sorbitan tristearate, steareth-100, and PEG-100 stearate; Suncaps 903 (Particle Sciences, Inc.), which includes ethylhexyl methoxycinnamate, benzophenone-3, synthetic beeswax, PEG-20, copernicia cerifera (carnauba) wax, Bis-PEG-12 dimethicone, beeswax, VP/Eicosene copolymer, sorbitan tristearate, steareth-100, and PEG-100 stearate; UV Pearls OMC (Sol Gel Technologies), which includes ethylhexyl methoxycinnamate, and silica; OMC-BMDBM (Sol Gel Technologies), which includes ethylhexyl methoxycinnamate, butyl methoxydibenzoylmethane, and silica; Tinosorb S Aqua (BASF), which includes, bis-ethylhexyloxyphenol methoxyphenyl triazine, and polymethyl methacrylate; Hybrid ABOS (Kobo), which includes, polymethylmethacrylate, butyl methoxydibenzoylmethane, and octyl salicylate; and Hybrid ABOMC (Kobo), which includes polymethylmethacrylate, butyl methoxydibenzoylmethane, and ethylhexyl methoxycinnamate.

Dimethicone

The present composition may comprise from about 2% to about 45%, preferably from about 3% to about 40%, more preferably from about 4% to about 30%, yet more preferably from about 4.5% to about 20%, and most preferably from about 4.5% to about 10%, for example about 3%, about 3.5%, about 4%, about 4.5%, about 5%, about 5.5%, about 6%, about 6.5%, about 7%, about 7.5%, about 8%, about 8.5%, about 9%, about 9.5%, about 10% or any ranges therebetween, by weight of the composition, of dimethicone. Particularly, the dimethicone may be a single dimethicone or a blend of two or more dimethicones disposed in the oil phase of the composition. Preferably, dimethicone in the composition of the present disclosure is a low-viscosity dimethicone. In some embodiments, dimethicone in the composition of the present disclosure is non-volatile.

As used herein, the term of "dimethicone" means a polydimethylsiloxane compound having the formula:

Dimethicone may be manufactured in multiple viscosities depending on the molecular mass, ranging from around 0.5 cSt to 20 million cSt. Particularly, dimethicone is in the form of a thin pourable liquid when the molecular mass is very low, and in the form of a thick rubbery semi-solid when the molecular mass is very high. Low-viscosity dimethicone are commonly used in skin care compositions as carriers for delivering a wide range of ingredients to skin without leaving a heavy, greasy feel. However, it has also some disadvantages, for example such low-viscosity dimethicone may be perceived as dry. As used herein, the term of "low-viscosity dimethicone" means a dimethicone having a relatively low kinematic viscosity, preferably no more than about 1000 cSt, and more preferably no more than about 500 cSt.

It was surprisingly discovered by the inventors of the present invention that a high SPF UV composition with an unexpectedly well-balanced skin feel could be formed by using a low-viscosity dimethicone in combination with other ingredients such as particulate materials.

The kinematic viscosity of the dimethicone which is useful in the composition of the present disclosure may be within the range of from about 0.5 cSt to about 1000 cSt, preferably from about 1 cSt to about 500 cSt, more preferably from about 1.5 cSt to about 350 cSt, yet more preferably from about 2 cSt to about 200 cSt, yet more preferably from about 3.5 cSt to about 100 cSt, yet more preferably from about 3.5 cSt to about 50 cSt, and most preferably from about 3.5 cSt to about 20 cSt, for example about 0.5 cSt, about 0.65 cSt, about 1 cSt, about 1.5 cSt, about 2 cSt, about 2.5 cSt, about 3 cSt, about 3.5 cSt, about 4 cSt, about 4.5 cSt, about 5 cSt, about 6 cSt, about 7 cSt, about 8 cSt, about 9 cSt, about 10 cSt, about 12 cSt, about 15 cSt, about 18 cSt, about 20 cSt, about 30 cSt, about 40 cSt, about 50 cSt, about 100 cSt, about 200 cSt, about 300 cSt, about 400 cSt, about 500 cSt or any ranges therebetween, as measured by the Rheology Method. Without intending to be bound by theory, it is believed that preferred concentrations of dimethicone and/or preferred kinematic viscosity of dimethicone may bring about additional benefits, such as higher stability, even better sensory benefits, suitable moisturization perception and/or product aesthetics. More particularly, it may help to stabilize the formula when exposed to low temperature conditions and prevents destabilization caused by other ingredients (for example the particulate material).

Particularly useful low-viscosity dimethicone include Andisil® SF 5, Andisil® SF 50, Andisil® SF 500, Andisil® SF 1000, Clearco PSF 0.65 cSt, PSF 1.5 cSt, PSF 2 cSt, Dow Corning 200® Fluid 0.65cs, Dow Corning 200® Fluid 1.5cs, Dow Corning Xiameter PMX-200 silicone fluid 5 cst, Dow Corning 200® Fluid 10 cSt, GE SF96-5, GE SF96-10cs, GE SF96-20cs, Momentive SF96-5, Momentive SF96-10, Momentive SF96-20, Rhodorsil 47V5, Rhodorsil 47V10, Rhodorsil 47V20, Shinetsu DM5, Shinetsu DM10, Shinetsu DM20.

Particulate Material

The compositions of the present invention may comprise from about 3% to about 45%, preferably from about 3.5% to about 40%, more preferably from about 4% to about 30%, yet more preferably from about 4.5% to about 20%, and most preferably from about 4.5% to about 10%, for example about 3%, about 3.5%, about 4%, about 4.5%, about 5%, about 5.5%, about 6%, about 6.5%, about 7%, about 7.5%, about 8%, about 8.5%, about 9%, about 9.5%, about 10% or any ranges therebetween, by weight of the composition, of a particulate material (also called cosmetic powder or dry powder).

Non-limiting examples of suitable particulate materials include inorganic powders, organic powders, composite powders, optical brightener particles, and mixtures of any of the foregoing. These particulates can, for instance, be platelet shaped, spherical, elongated or needle-shaped, or irregularly shaped; surface coated or uncoated; porous or non-porous; charged or uncharged. In some embodiments, the particulate material is hydrophobically coated.

Suitable inorganic particulate materials include, but are not limited, to talc, silicates, silica, iron oxides, titanium dioxides, zinc oxides and any mixtures thereof.

Suitable organic particulate materials include, but are not limited, to polymeric particles chosen from the methylsilsesquioxane resin microspheres, for example, Tospearl™ 145A, Tospearl™ CF600; microspheres of polymethylmethacrylates, for example, Micropearl™ M 100 (Seppic); the spherical particles of crosslinked polydimethylsiloxanes, for example, Trefil™ E 506C or Trefil™ E 505C (Dow Corning Toray Silicone); spherical particles of polyamide, for example, nylon-12, and Orgasol™ 2002D Nat C05 (Atochem); polystyrene microspheres, for example Dyno Particles, sold under the name Dynospheres™, and ethylene acrylate copolymer, sold under the name FloBead™ EA209 (Kobo); aluminium starch octenylsuccinate, for example Dry Flo™ (Akzo Nobel); starch for example tapioca starch, distarch phosphate, tapioca starch, acetyl substituted starch, adipic acid substituted starch, hydroxypropylated starch, corn starch, 2-hydropropylether modified starch, hydroxypropyl starch phosphate ester; cyclodextrins and derivatives thereof; polymethyl silsesquioxane coated tapioca particles, for example Dry Flo TS™ (Akzo Nobel); microspheres of polyethylene, for example Microthene™ FN510-00 (Equistar), silicone resin, polymethylsilsesquioxane silicone polymer, platelet shaped powder made from L-lauroyl lysine, and mixtures thereof.

Particularly, the particulate material may be selected from the group consisting of sugar derivatives, silica, silicates, carbonates, silicones and any mixtures thereof. More particularly, the sugar derivatives may be selected from the group consisting of aluminium starch octenylsuccinate, distarch phosphate, tapioca starch, acetyl substituted starch, adipic acid substituted starch, hydroxypropylated starch, corn starch, 2-hydropropylether modified starch, hydroxypropyl starch phosphate ester, cyclodextrins and derivatives thereof, polymethylsilsesquioxane-coated starch such as polymethylsilsesquioxane-coated tapioca starch, and any combinations thereof; and/or the silicates may be selected from talc, kaolin and a combination thereof; and/or the carbonates may be selected from magnesium carbonate, calcium carbonate and a combination thereof; and/or the silicone may be are selected from vinyl dimethicone/methicone silsesquioxane crosspolymer, polysilicone, polymethylsilsesquioxane, diphenyl dimethicone/vinyl diphenyl dimethicone/silsesquioxane crosspolymer, and any combinations thereof.

In some embodiments, the average diameter of the longest side of the individual particles of particulate materials is within the range of between about 1 micron and about 150 microns, preferably less than about 75 microns, and more preferably less than about 50 microns, for example about 1 micron, about 2 micron, about 3 micron, about 4 micron, about 5 micron, about 1 micron, about 10 micron, about 15 micron, about 30 micron, or any ranges therebetween.

Weight Ratio Between Low-Viscosity Dimethicone and Particulate Material

In some embodiments, the weight ratio of the dimethicone to the particulate material in the skin care composition is between about 1:2 and about 2:1, preferably between about 1:1.5 and about 1.5:1, more preferably between about 1:1.2 and about 1.2:1, and most preferably between 1:1.1 and 1.1:1, for example about 1:2, about 1:1.8, about 1:1.5, about 1:1.3, about 1:1.2, about 1:1.1, about 1:1.05, about 1:1, about 1.05:1, about 1.1:1, about 1.2:1, about 1.3:1, about 1.5:1, about 1.8:1, about 2:1, or any ranges therebetween.

Without intending to be bound by theory, it is believed that preferred concentrations and/or preferred types of dimethicone (for example dimethicone, 5 cSt) and particulate materials (for example polymethylsilsesquioxane or polymethylsilsesquioxane-coated starch) and/or preferred ratio of dimethicone to particulate materials (for example between 1:1.1 and 1.1:1) may bring about additional benefits, such as higher stability, even better sensory benefits, suitable moisturization perception and/or product aesthetics.

Fatty Alcohol

The compositions of the present disclosure may comprise one or more fatty alcohols. Fatty alcohols typically include monohydric alcohols having 8-22 carbon atoms although longer chain alcohols in excess of 30 carbons may be used. The fatty alcohols may be saturated or unsaturated. The fatty alcohols may be straight or branched. In particular, the compositions may comprise straight chain, saturated fatty alcohol with a terminal hydroxyl. Suitable fatty alcohols include decyl alcohol, lauryl alcohol, myristyl alcohol, cetyl alcohol, stearyl alcohol, isostearyl alcohol, cetearyl alcohol, icosyl alcohol, behenyl alcohol and the like. The phase may comprise from about 0.1%, 0.5%, 1%, 1.5%, 2%, 3%, 5% to about 5%, 7.5%, 10%, 15%, 20% of fatty alcohol.

Alternatively, the compositions of the present disclosure may be essentially free of one or more or any fatty alcohols. Particularly, the compositions of the present disclosure may be essentially free of a fatty alcohol selected from the group consisting of cetyl alcohol, stearyl alcohol, cetearyl alcohol, behenyl alcohol, and any combinations thereof.

In the context of the present disclosure, the expression of "essentially free of" means that the concentration, by weight of the composition, of an ingredient is no more than about 1%, preferably about 0.8%, more preferably about 0.5%, yet more preferably about 0.3%, yet more preferably about 0.2%, yet more preferably about 0.1%, and most preferably about 0.01%.

In some embodiments, the composition comprises from 0% to about 0.5%, preferably from 0% to about 0.2%, yet more preferably from 0% to about 0.1%, yet more preferably from 0% to about 0.05%, and most preferably from 0% to about 0.01%, for example 0%, about 0.01%, about 0.05%, about 0.1%, about 0.2%, about 0.3%, about 0.4%, about 0.5% or any ranges therebetween, by weight of the composition, of a fatty alcohol.

Without intending to be bound by theory, it is believed that the absence of fatty alcohols in the skin care composition may bring about additional benefits, such as higher stability, even better sensory benefits, suitable moisturization perception and/or product aesthetics.

Emulsifier

The compositions of the present disclosure may further comprise from about 0.01% to about 40%, by weight of the composition, of an emulsifier. Emulsifiers may be nonionic, anionic or cationic.

Suitable emulsifiers may be selected from the group consisting of ether-based emulsifiers, ester-based emulsifiers, polymeric emulsifiers, silicone emulsifiers, and any combinations thereof.

The ether-based emulsifiers may be selected from the group consisting of ethers of polyglycols and of fatty alcohols, ethers of polyglycols and of glycosylated fatty alcohols, ethers of $C_{12-30}$ alcohols and of glycerol or polyglycerol, ethers of oxyalkylene-modified $C_{12-30}$ alcohols and of glycerol or polyglycerol, ethers of $C_{12-30}$ fatty alcohols and of sucrose or glucose, ethers of sorbitol and/or sorbitan and of alkoxylated sorbitan, ethers of polyglycols and of cholesterol, and any combinations thereof.

The ester-based emulsifiers may be selected from the group consisting esters of polyglycols and of fatty acids, esters of polyglycols and of glycosylated fatty acids, esters of $C_{12-30}$ fatty acids and of glycerol or polyglycerol, esters of sucrose or glucose and of $C_{12-30}$ fatty acids, esters of pentaerythritol and of $C_{12-30}$ fatty acids, esters of sorbitol and/or sorbitan and of $C_{12-30}$ fatty acids, esters of $C_{12-30}$ fatty acids and of alkoxylated ethers of sorbitol and/or sorbitan, and any combinations thereof.

Nonlimiting examples of emulsifiers for use herein may include: polyethylene glycol 20 sorbitan monolaurate (polysorbate 20), steareth-20, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, polyoxyethylene 20 sorbitan trioleate (polysorbate 85), sorbitan monolaurate, polyoxyethylene 4 lauryl ether sodium stearate, polyglyceryl-4 isostearate, hexyl laurate, PPG-2 methyl glucose ether distearate, ceteth-10, diethanolamine cetyl phosphate, glyceryl stearate, PEG 40 hydrogenated castor oil, PEG-60 hydrogenated castor oil, Glycereth-25 PCA Isostearate, and mixtures thereof.

Silicone emulsifiers may be useful. Linear or branched type silicone emulsifiers may also be used. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin Etsu.

Polymeric emulsifiers may also be used. Preferably, the composition may comprise from about 0.02% to about 30%, from about 0.03% to about 20%, from about 0.05% to about 5%, more preferably from about 0.1% to about 2%, yet more preferably from about 0.2% to about 1%, and most preferably from about 0.3% to about 0.8%, for example, about 0.3%, about 0.35%, about 0.4%, about 0.45%, about 0.5%, about 0.55%, about 0.6%, about 0.65%, about 0.7%, about 0.75%, about 0.8% or any ranges therebetween, by weight of the composition, of a polymeric emulsifier.

Preferred polymeric emulsifier may be selected from the group consisting of crosslinked alkyl acrylates, acryloyldimethyltaurate polymers, and any combinations thereof. Crosslinked alkyl acrylates are crosslinked polymers in which the co-monomers consist of at least one of the following: acrylic acid, sodium acrylate, methacrylic acid, or alkyl acrylate, and acryloyldimethyltaurate polymers mean homopolymers, copolymers or crosslinked polymers, the monomers of which are at least partially composed of acryloyldimethyltaurate monomers.

Particularly, the crosslinked alkyl acrylates are selected from the group consisting of acrylates/C10-30 alkyl acrylate crosspolymer, acrylates/C12-13 alkyl methacrylates/methoxyethyl acrylate crosspolymer, acrylates crosspolymer, acrylates/ethylhexyl acrylate crosspolymer, acrylates/ethylhexyl acrylate/glycidyl methacrylate crosspolymer, acrylates/PEG-4 dimethacrylate crosspolymer, acrylates/Steareth-20 methacrylate crosspolymer, acrylates/vinyl isodecanoate crosspolymer, acrylates/vinyl neodecanoate crosspolymer, allyl methacrylate/glycol dimethacrylate crosspolymer, allyl methacrylates crosspolymer, butyl acrylate/glycol dimethacrylate crosspolymer, C8-22 alkyl acrylates/methacrylic acid crosspolymer, glycol dimethacrylate/vinyl alcohol crosspolymer, lauryl methacrylate/glycol dimethacrylate crosspolymer, lauryl methacrylate/sodium methacrylate crosspolymer, methacrylic acid/PEG-6 methacrylate/PEG-6 dimethacrylate crosspolymer, PEG/PPG-5/2 methacrylate/methacrylic acid crosspolymer, stearyl/lauryl methacrylate crosspolymer, and any combinations thereof; and/or the acryloyldimethyltaurate polymers may be selected from the group consisting of acrylamide/Sodium acryloyldimethyltaurate copolymer, acrylamide/sodium acryloyldimethyltaurate/acrylic acid copolymer, ammonium acryloyldimethyltaurate/beheneth-25 methacrylate crosspolymer, ammonium acryloyldimethyltaurate/carboxyethyl, acrylate crosspolymer, ammonium acryloyldimethyltaurate/Laureth-7 methacrylate copolymer, ammonium acryloyldimethyltaurate/Steareth-25 methacrylate crosspolymer, ammonium acryloyldimethyltaurate/Steareth-8 methacrylate copolymer, ammonium acryloyldimethyltaurate/vinyl formamide copolymer, ammonium acryloyldimethyltaurate/VP copolymer, ammonium polyacryloyldimethyl taurate dimethylacrylamide/sodium acryloyldimethyltaurate crosspolymer, HEA/sodium acryloyldimethyltaurate/Steareth-20 methacrylate copolymer, hydroxyethyl acrylate/sodium acryloyldimethyl taurate copolymer, polyacryloyldimethyltaurate polyoxymethylene melamine, sodium acrylate/acryloyldimethyltaurate/dimethylacrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate crosspolymer, sodium acryloyldimethyl taurate/acrylamide/VP copolymer, sodium acryloyldimethyltaurate/VP crosspolymer, sodium polyacryloyldimethyl taurate and any combinations thereof.

Non-limiting examples of polymeric emulsifiers are Carbopol 1382™, Carbopol Ultrez 20™, Carbopol Ultrez 21™, Pemulen TR II™, Pemulen TR I™, Pemulen EZ4U™, Aculyn 88, Aculyn 38, Stabylen 30, Aqua Keep 10SH-NFC, Aristoflex® AVC, SEPINOV™ EMT 10, SIMULGEL™ NS, SEPIPLUS™ S, EMT polymer, and the like.

In some preferred embodiments, the composition of the present disclosure comprises acrylates/C10-30 alkyl acrylate crosspolymer and/or hydroxyethyl acrylate (and) sodium acryloyldimethyl (and) taurate copolymer. The use of such polymeric emulsifiers surprisingly provides additional sensory benefits. Without intending to be bound by theory, it is believed that they function also as thickeners to prevent use of other thickeners/emulsifiers that may negatively impact on the sensory perception of the product, and in other words, they can emulsify oil and water and also thicken the composition by the use of a single material.

Without intending to be bound by theory, it is believed that that preferred concentrations and/or preferred types of the emulsifier bring about additional benefits, such as higher stability, even better sensory benefits, suitable moisturization perception, more cost-effective and/or product aesthetics.

PH Adjuster

The composition of the present disclosure may further comprise a pH adjuster to control the pH of the composition. Particularly, the pH of the composition of the present disclosure is within the range of from about 5 to about 8, preferably from about 5.2 to about 7.8, and more preferably from about 5.4 to about 7.6, for example about 5.4, about 5.6, about 5.8, about 6.0, about 6.2, about 6.4, about 6.6, about 6.8, about 7.0, about 7.2, about 7.4, about 7.6 and any ranges therebetween.

Particularly, the composition may further comprise from about 0.01% to about 5%, preferably from about 0.1% to about 3%, more preferably from about 0.3% to about 2%, yet more preferably from about 0.4% to about 1.8%, and most preferably from about 0.5% to about 1.6%, for example about 0.4%, about 0.5%, about 0.6%, about 0.7%, about 0.8%, about 0.9%, about 1.0%, about 1.1%, about 1.2%, about 1.3%, about 1.4%, about 1.5%, about 1.6% and any ranges therebetween, by weight of the composition, of a pH adjuster, wherein said pH adjuster is selected from the group consisting of potassium hydroxide, sodium hydroxide, ammonium hydroxide, aminomethyl propanol, triethanolamine, tetrahydroxypropyl ethylene diamine and any combinations thereof.

When a polymeric emulsifier and a pH adjuster is used, it is preferred, and sometimes necessary in the case of certain compositions, to formulate the composition of the present disclosure with the proper ratio of the polymeric emulsifier to the pH adjuster. In some embodiments, the weight ratio of the polymeric emulsifier to the pH adjuster is between about 1:5 and about 1:0.5, preferably between about 1:3 to about 1:1, for example about 1:3, about 1:2.5, about 1:2, about 1:1.5, about 1:1.1 and any ranges therebetween.

Without intending to be bound by theory, it is believed that that preferred concentrations and/or preferred types of the pH adjuster bring about a more preferred result, such as higher stability, even better sensory benefits, suitable moisturization perception, more cost-effective and/or product aesthetics.

Thickener

The composition of the present invention may further comprise a thickener (also called a thickening agent) or an additional thickener if the emulsifier in the composition also functions as a thickener. The composition of the present invention may comprise from about 0.1% to about 5%, or, alternatively, from about 0.2% to about 2%, of a thickener or an additional thickener when present. Suitable classes of thickeners include but are not limited to carboxylic acid polymers, polyacrylamide polymers, sulfonated polymers, copolymers thereof, hydrophobically modified derivatives thereof, and mixtures thereof.

One preferred thickener for use in the present invention is an acrylate cross linked silicone copolymer network (also sometimes referred to as "polyacrylate siloxane copolymer network"). Suitable thickening agents include carboxylic acid polymers, polyacrylamide polymers or copolymers, sulfonated polymers, gum, clays, cellulose or modified cellulosic compositions, and the like.

Other Optional Ingredients

The present composition may include a variety of optional ingredients that are known for use in personal care composition, as long as the optional ingredient(s) do not unduly alter product stability, aesthetics, or performance. The optional ingredients, when incorporated into the composition, should be suitable for contact with human keratinous tissue without undue toxicity, incompatibility, instability, allergic response, and the like within the scope of sound judgment. The compositions herein may comprise from about 0.0001% to about 50%; from about 0.001% to about 20%; or, alternately, from about 0.01% to about 10%, by weight of the composition, of optional ingredients. Some non-limiting examples of optional ingredients include abrasives, absorbents, opacifying agents, colorings/colorants (e.g., pigments, dyes, and lakes), particles, essential oils, anti-caking agents, foaming agents, anti-foaming agents, oil control agents, binders, biological additives, vitamins, minerals, peptides, sugar amines, flavonoid compounds, anti-oxidants, preservatives, plant extract, phytosterols, protease inhibitors, tyrosinase inhibitors, exfoliating agents, skin lightening agents, sunless tanning agents, anti-acne actives, anti-cellulite actives, anti-wrinkle actives, phytosterols and/or plant hormones, N-acyl amino acid compounds, antimicrobials, antifungals, moisturizers, emollients, humectants, lubricating agents, fragrances, anti-dandruff agents, buffering agents, bulking agents, chelating agents, biocides, denaturants, astringents, external analgesics, anti-inflammatory agents, sunscreen agents, film formers and/or polymers for aiding film-forming properties and substantivity of the composition, propellants, reducing agents, sequestrants, conditioning agents, and combinations of these.

In some embodiments, the compositions of the present disclosure may be essentially free of ethanol. Without intending to be bound by theory, it is believed that that the absence of ethanol in the compositions of the present disclosure brings about a more preferred result, such as even better sensory benefits and/or product aesthetics.

In some particular embodiments, the present disclosure provides a composition comprising:

a) from 20% to 45%, by weight of the composition, of one or more UV-blocking actives that phenylbenzimidazole sulfonic acid, homosalate, octocrylene, and butyl methoxydibenzoylmethane, in which the concentration of phenylbenzimidazole sulfonic acid is from 2% to 5% by weight of the composition, the concentration of homosalate is from 6% to 10% by weight of the composition, the concentration of octocrylene is from 7% to 11% by weight of the composition, and the concentration of butyl methoxydibenzoylmethane is from 1% to 5% by weight of the composition;

b) from 4.5% to 6%, by weight of the composition, of a dimethicone having a kinematic viscosity of from 3.5 cSt to 20 cSt as measured by the Rheology Method;

c) from 4.5% to 6%, by weight of the composition, of polymethylsilsesquioxane-coated starch or polymethylsilsesquioxane;

d) from 0.3% to 0.8%, by weight of the composition, of an acrylates/C10-30 alkyl acrylate crosspolymer; and e) from 0.5% to 0.8%, by weight of the composition, of sodium hydroxide.

Test Methods

Test 1: Tack Method

This method provides a suitable means for determining the stringiness of a sample composition being tested. The method uses a texture analyzer to contact a probe with a film formed from the sample composition. The texture analyzer then measures the force needed to separate the probe from the sample composition film. Tack Force, Time Weighted Force Area, Mean Break Time, and the change in Break Time can all be determined by this method. The Tack Method is configured to run for a period of 100 minutes. It is believed, without being limited by theory, that the stringiness properties exhibited by a sample composition over the course of the Tack Test approximate the stringiness properties exhibited by the composition during the first few minutes (e.g., less than 10 minutes, between 30 seconds and 5 minutes, or between 1 minute and 3 minutes) of use of the sample composition by a user.

Figure 1:
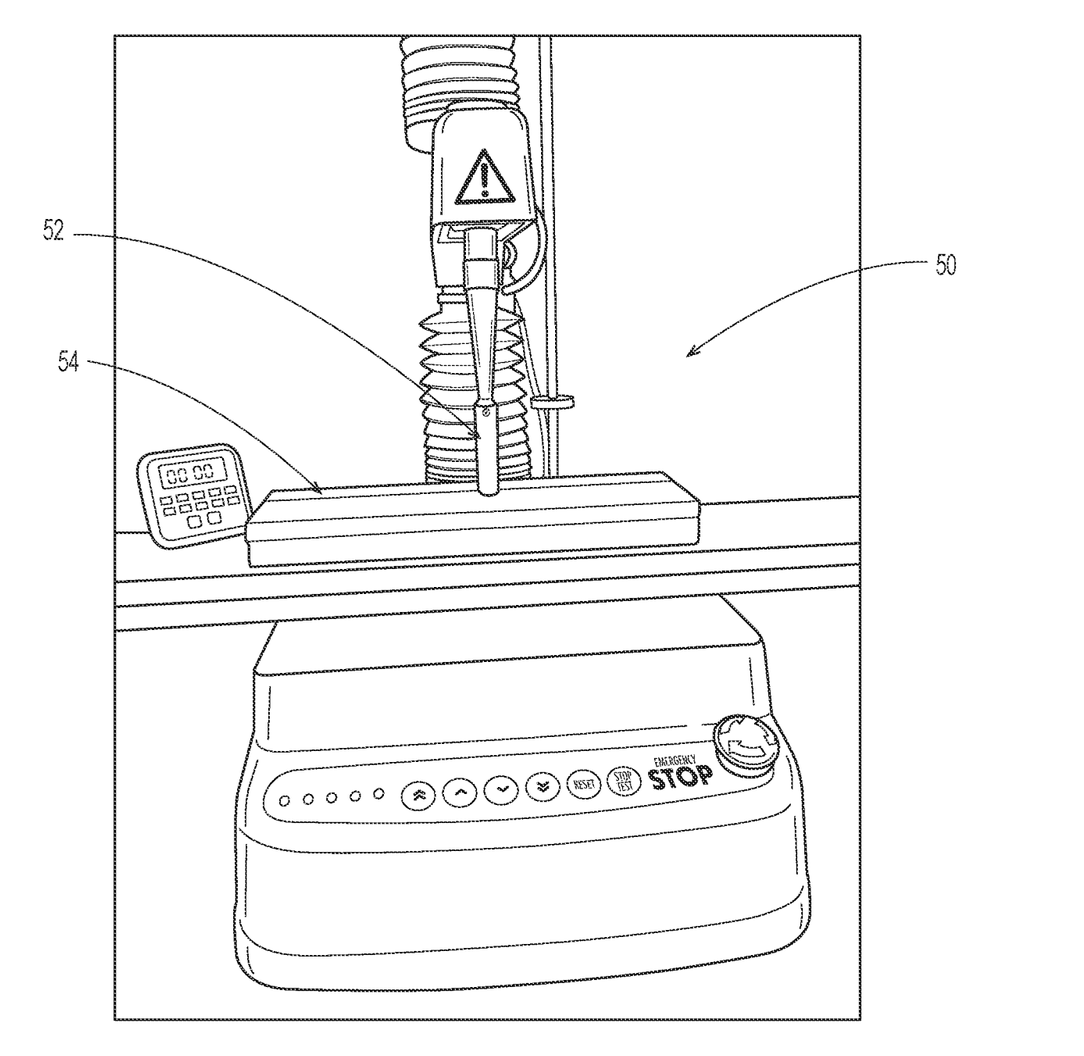
The FIG. illustrates an experimental setup for the Tack Method.

FIG. 1 illustrates an exemplary test setup for the Tack Test. A TA.XT2i brand texture analyzer (available from Texture Technologies Corporation, MA) 50 or equivalent is used to measure the tack of a film formed from a sample composition. The texture analyzer is equipped with a tack probe 52 in the form of a 12.75 mm diameter acrylic cylinder with a flat surface. During testing, the flat surface of the probe 52 is contacted with the surface of a film of the composition. Thus, the flat surface of the probe and the surface of the film must be parallel to one another during testing to ensure there is sufficient contact by the film across the effective test surface of the probe 52. The film is made by filling or overfilling (followed by draw down) a rectangular channel 54 (e.g., 25 cm long×30 mm wide×a 0.25 mm deep) with the composition to be tested.

The test is conducted using an adhesive test protocol with a pretest speed of 0.10 mm/second, a test speed of 0.10 mm/sec and a post-test speed of 1.0 mm/sec. The applied force is 200 g, the return distance is 4 mm and the contact time is 5.0 sec. The trigger type to designate sample contact is set to automatic and the trigger force is 5.0 g. The test is run and at the following time increments immediately after the film is prepared: <1 minute (i.e., immediately following preparation of the film), 10, 20, 30, 40, 50, 60, 80, and 100 minutes. Each time point is run on a previously undisturbed/untested area of the sample. Each sample is run in triplicate and the averages are recorded.

Data extraction uses the portion of data that is collected as the probe pulls upward out of the sample. The Tack Force is the peak force of each test run.

Time weighted force area is determined by the following formula:

$$\text{time weighted force area} = (t1 - t2) * \left[\frac{P1 - P2}{200}\right] * [(t1 | t2)/2]$$

Where:
t1=the later of the two times in the time range at which the measurement was taken;
t2=the earlier of the two times in the time range at which the measurement was taken;
P1=peak force in grams at time 1 in the pair of times being calculated; and
P2=peak force in grams at time 2 in the pair of times being calculated.

When calculating the difference between t1 and t2 or P1 and P2, the absolute value of the result is used to calculate time weighted force area. Time Weighted Force Area is reported as the sum of the individual time weighted force area values calculated for each of the 8 time intervals (<1 min to 10 min, 10 min to 20 min, 20 min to 30 min, etc.).

Break Time is determined by the width of the force curve. The start time of the Break Time calculation is when the sign of the force exerted by the texture analyzer changes to positive from negative at time zero (i.e., the start of the test) and the time at which the force decays back to 0.0+/−0.02 from the peak force as the break time. Mean Break Time is reported as the average of the break times at 60, 80 and 100 minutes. The change in Break Time is the difference between the initial Break time and the Break time at 100 minutes.

Test 2: Rheology Method

This method provides a suitable means of measuring the dynamic viscosity at a given shear rate. The instrument used in this method is a Discover HR-2 rheometer, available from TA Instruments, or equivalent. The instrument is set up to conduct a rotational ramp under controlled stress conditions, from 0 to 800 Pa over 240 seconds, using a cross hatched parallel plate geometry with a 40 mm diameter, and a 0.9 mm gap. The temperature is set to 25° C. The instrument protocol is set up to collect 100 data points in a logarithmic distribution.

After conducting an automated calibration, approximately 5 grams of a sample is placed on the center of the plate. The plate is positioned to provide a gap of 09 mm, and any excess material squeezed out of the perimeter gap is carefully trimmed away. Then the measurement is initiated. At the end of the run, the data file is saved for subsequent plotting and analysis. The dynamic viscosity is reported as the value in Pa*S at or near shear stress of 100 $S^{-1}$. Kinematic viscosity can by calculated by dividing the measured dynamic viscosity by the density of the sample at 25° C.

Examples

Example 1: Improved Balance Between Stringiness and Viscosity Achieved by the Compositions of the Present Disclosure Compared to Conventional Products Four sample skin care compositions (Composition Examples 1 to 4, Ex.1 to 4) are prepared as follows. In a suitable vessel, the water phase ingredients are combined and heated to 35° C. In a separate suitable vessel, the oil phase ingredients are combined and heated to 65° C. Then the thickener is added to the oil phase. Next the oil phase ingredients are added to the water phase ingredients, and the resulting emulsion is milled (e.g., with a rotor-stator mill). The emulsion is cooled to 45° C. while stirring. At 45° C., the remaining ingredients, including neutralized phenylbenzimidazole sulfonic acid and additional neutralizer are added. The product is then cooled with stirring to 30° C. The cooled product is milled again, and then poured into suitable containers. Detailed compositional breakdown of these compositions are listed as follows (see Table 1).

TABLE 1

|  |  | Ex. 1 | Ex. 2 | Ex. 3 | Ex. 4 |
|---|---|---|---|---|---|
|  | Water | qs | qs | qs | qs |
| Oil phase UV-blocker | Diethylamino Hydroxybenzoyl Hexyl Benzoate | — | — | 4 | — |
| Oil phase UV-blocker | Bemotrizinol | — | — | 2 | — |
| Oil phase UV-blocker | Ethylhexyl Methoxycinnamate | — | — | 7.5 | — |
| Oil phase UV-blocker | Homosalate | 8 | 8 | — | 8 |
| Oil phase UV-blocker | Octocrylene | 9 | 9 | — | 9 |
| Oil phase UV-blocker | Butyl Methoxydibenzoylmethane | 3 | 3 | — | 3 |
| Water phase UV-blocker | Phenylbenzimidazole Sulfonic Acid | 3 | 3 | 3 | 3 |
| Thickener/Emulsifier | Acrylates/C10-30 Alkyl Acrylate Crosspolymer[1] | 0.4 | 0.5 | 0.5 | 0.5 |
| Neutralizer | NaOH | — | 0.66 | — | — |
| Neutralizer | Amino Methyl Propanol | 1.268 | — | 1.351 | 1.351 |
| Low-viscosity dimethicone | Dimethicone (5 cSt)[2] | 5 | 5 | 2 | 2 |
| Particulate | Polymethylsilsesquioxane[3] | 5 | 5 | — | — |
| Particulate | Tapioca Starch (and) Polymethylsilsesquioxane[4] | — | — | 5 | 5 |
|  | Ethyl Alcohol | — | — | 10 | 10 |
| Chelant (water phase) | Disodium EDTA | — | 0.1 | — | — |
| Preservative (water phase) | 1,2-Hexanediol and 1,2-Octanediol | 0.800 | 0.800 | 0.800 | 0.800 |
| Preservative (water phase) | Phenoxyethanol | 0.375 | 0.375 | 0.375 | 0.375 |

[1]Pemulen TR II available from Lubrizol.
[2]Xiameter ® PMX-200 silicone fluid 5cs from Dow Corning
[3]Tospearl CF600 from Momentive
[4]Dry Flo TS from AkzoNobel The dynamic viscosity of each composition at the shear rate of 100 $S^{-1}$ was determined according to the Rheology Method described in Test 2 hereinabove, and the Mean Break Time values were determined according to the Tack Method described in Test 1 hereinabove. Then, the Mean Break Time and dynamic viscosity of the sample compositions according to the present disclosure were compared to some conventional skin care products (Comparative Composition Examples A to H, Compar. Ex. A to H) marketed as providing sensory benefits. The Mean Break Time values and dynamic viscosity values are shown in Table 2. As can be seen in Table 2, the present compositions provide an advantageous balance between stickiness/stringiness (indicated by Mean Break Time) and spreadability (indicated by dynamic viscosity). In vivo SPF for the compositions of the present disclosure was tested and also shown in Table 2.

Some examples (Ex.1 and Ex.2) were monitored for emulsion stability and the stabilization of active ingredients for a period of 12 weeks at 25° C. and 40° C. The results show they are stable.

TABLE 2

| Composition | Tested/Labeled/ Expected SPF | Average Break Time (s) | Dynamic Viscosity at 100 $s^{-1}$ (Pa · S) |
|---|---|---|---|
| Ex. 1 | 50+ | 0.20 | 0.65 |
| Ex. 2 | 50+ | 0.24 | 0.50 |
| Ex. 3 | 50+ | 0.11 | 0.47 |
| Ex. 4 | 50+ | 0.16 | 0.42 |
| Compar. Ex. A[1] | 50+ | 0.16 | 0.89 |
| Compar. Ex. B[2] | 50+ | 0.16 | 1.40 |
| Compar. Ex. C[3] | 50+ | 0.18 | 0.73 |
| Compar. Ex. D[4] | 50 | 0.24 | 1.12 |
| Compar. Ex. E[5] | 50+ | 0.78 | 0.21 |
| Compar. Ex. F[6] | 50+ | 0.74 | 0.20 |
| Compar. Ex. G[7] | 50+ | 0.80 | 0.25 |
| Compar. Ex. H[8] | 50 | 0.84 | 0.13 |

[1]Biore Aqua UV Rich Watery Essence SPF 50 SPF50+ (T0000576 & T0000636).
[2]Biore Aqua UV Rich Watery Essence SPF 50 SPF50+ PA++++ (T0002507)
[3]Lancome UV Expert XL Shield Aqua Gel SPF 50: 20181015
[4]Lancome UV Expert Youth Shield Aqua Gel SPF50 PA++++ (78P800)
[5]Anessa Perfect UV Sunscreen Aqua Booster SPF 50+ (6106K, 6097EB & 6096EB)
[6]Anessa Perfect UV Sunscreen Aqua Booster SPF50+ PA+++ (6249LB)
[7]Anessa Perfect UV Sunscreen Skincare Milk SPF50+ PA++++ (8017QD)
[8]Shiseido Perfect UV Protector 50+ Wet Force Multi-Defense SPF50+ PA++++ (8006KN)

Example 2: Improved Skin Feels Achieved by the Compositions of the Present Disclosure Compared to Conventional Products in Single Product Blind Test (SPBT) and Panel Test

SPBT

In this study, the compositions of the present disclosure and comparative compositions were placed with 500 women (base size=100 for each leg). Each consumer uses 1 product daily for 10 days, with recall questionnaires before the study, on Day 1. Products were blinded and placed in identical white tubes (except for sprays and shake-well products, which were simply blinded) but placed under a UV-Blocker context ("Daily UV Blocker").

Consumer Profile: Chinese females, Age 25-54, living in Beijing/Shanghai who use UV blocker every day during summer.

As part of the study, products were rated overall on a 5-pt scale (Poor, Fair, Good, Very Good and Excellent) which was converted to a 0-100 scale for analysis and on sensory attributes. Details are shown below on Day 1 scores which reflect first-time use delight from users.

As shown in Table 3, the compositions of the present disclosure show significantly better feels than comparative compositions. Particularly, both the difference of overall ratings between Ex. 3 and comparative examples and the difference between Ex. 4 and comparative examples are statistically significant (p>0.05).

TABLE 3

| Day 1 scores (0-100, from a 5 pt scale of Poor-Excellent) | Ex. 3 | Ex. 4 | Compar. Ex. B[1] | Compar. Ex. F[2] | Compar. Ex. D[3] |
|---|---|---|---|---|---|
| Statistical grouping | A | B | C | D | E |
| Overall rating | 79 CDE[4] | 77 CDE | 70 E | 67 | 65 |
| Not leaving skin greasy feels | 78 dE | 72 | 79 BdE | 72 | 68 |
| Not leaving skin sticky/tacky feels | 77 bdE | 71 | 78 BdE | 72 | 66 |
| Not leaving skin shiny | 80 BCDE | 69 E | 71 E | 68 e | 63 |
| Leaving skin refreshed feels | 77 BDE | 71 DE | 73 DE | 64 | 63 |

[1]Biore Aqua UV Rich Watery Essence SPF 50 SPF50+ PA++++ (T0002507)
[2]Anessa Perfect UV Sunscreen Aqua Booster 5PF50+ PA+++ (6249LB)
[3]Lancome UV Expert Youth Shield Aqua Gel SPF50 PA++++ (78P800)
[4]Capital letters denote a significant difference at p > 0.05, and small letters denote a significant difference at p > 0.1

Panel Test

In this study, the products were blinded and placed among 10 trained panelists, who were using the products at randomized sequences to give objective quantitative assessment of the product. The panelists scored the sensory feels on a −5 to +5 scale, in which stickiness, oil amount, shining are considered as negative feels, and spreadability and water-like feel are desirable feels.

Each of the panelists used the composition of Ex. 2, Ex. 3, and Ex. 4 on their face and rate the product at different timepoints. Overall, Ex. 2 is even better than Ex. 3 and Ex. 4 in all aspects as tested.

TABLE 4

| DQs | Statistical Grouping | Immediate Spreadability | Oil Amount | Water-like Feel | Stickiness |
|---|---|---|---|---|---|
| Ex. 3 | A | 1.6 | −1.8 | 1.8 | −2.2 |
| Ex. 4 | B | 1 | −1.2 | 2.1 | −1.4 |
| Ex. 2 | C | 2.8 | −2.5 | 3 | −2.8 |
| Statistics* | | A and C B and C | A and C B and C | A and C B and C | A and B B and C |

| DQs | Statistical Grouping | 15 mins Oil Amount | Stickiness | Refresh Feeling | Shining |
|---|---|---|---|---|---|
| Ex. 3 | A | −3.5 | −3.4 | 3.4 | 0.5 |
| Ex. 4 | B | −2.6 | −2.7 | 2.8 | 0.6 |
| Ex. 2 | C | −3 | −3.1 | 3 | 0.3 |
| Statistics | | A and B | A and B | | |

*It indicates which two groups among Groups A, B and C show a significant difference at 90% confidence level.

Example 3: Improved Skin Feels Achieved by the Combination of Dimethicone and Particulate Material Four sample skin care compositions are prepared as described above, which include: (Ex. 2) 5% dimethicone+5% particulate material; (Compar. Ex. 1) 1% dimethicone+5% particulate material; (Compar. Ex. 2) 5% dimethicone+1% particulate material; and (Compar. Ex. 3) 0% dimethicone+0% particulate material. Detailed compositional breakdown of these compositions are listed as follows.

TABLE 5

| | Ex. 2 | Compar. Ex. 1 | Compar. Ex. 2 | Compar. Ex. 3 |
|---|---|---|---|---|
| Water | qs | qs | qs | qs |
| Homosalate | 8 | 8 | 8 | 8 |
| Octocrylene | 9 | 9 | 9 | 9 |
| Butyl Methoxydibenzoylmethane | 3 | 3 | 3 | 3 |
| Phenylbenzimidazole Sulfonic Acid | 3 | 3 | 3 | 3 |
| Acrylates/C10-30 Alkyl Acrylate Crosspolymer[1] | 0.5 | 0.5 | 0.5 | 0.5 |
| NaOH | 0.66 | 0.66 | 0.66 | 0.66 |
| Dimethicone (5 cSt)[2] | 5 | 1 | 5 | — |
| Polymethylsilsesquioxane[3] | 5 | 5 | 1 | — |
| Disodium EDTA | 0.1 | 0.1 | 0.1 | 0.1 |
| 1,2-Hexanediol and 1,2-Octanediol | 0.800 | 0.800 | 0.800 | 0.800 |
| Phenoxyethanol | 0.375 | 0.375 | 0.375 | 0.375 |

[1]Pemulen TR II available from Lubrizol.
[2]Xiameter ® PMX-200 silicone fluid 5cs from Dow Corning
[3]Tospearl CF600 from Momentive Rheology and Tack Test The dynamic viscosity of each composition was determined according to the Rheology Method described in Test 2 hereinabove, and the Mean Break Time values were determined according to the Tack Method described in Test 1 hereinabove. The Mean Break Time values and dynamic viscosity values are shown in the table as below. The data shows that the present compositions provide a good balance between stickiness/stringiness (indicated by Mean Break Time) and spreadability (indicated by dynamic viscosity) by using preferred concentrations of dimethicone and particulate materials.

Panel Test

Similarly as above, the products were blinded and placed among 10 trained panelists, who were using the products at randomized sequences to give objective quantitative assessment of the product. The panelists scored the sensory feels on a −5 to +5 scale, in which stickiness, oil amount, oil feel are considered as negative feels (i.e., a high positive score indicates an undesirable effect). Each of them used these compositions on their face and rate the product at 15 minutes after application. The results prove that the present compositions provide an advantageous skin feels by using preferred concentrations of dimethicone and particulate materials. Especially, in the term of stickiness, the composition according to the present invention (Ex.2) shows significantly improved performance compared to the controls (Comparative Examples 1-3).

TABLE 6

| DQs | | Oil Amount | Oil Feel | Stickiness |
|---|---|---|---|---|
| Ex. 2 | 15 mins | 0.5 | 0.3 | −0.3 |
| Compar. Ex. 1 | | 0.4 | 0.4 | −0.1 |
| Compar. Ex. 2 | | 0.9 | 0.8 | 0.4 |
| Compar. Ex. 3 | | 1.9 | 1.8 | 1.7 |
| Scaling | | Less greasy (−5) More greasy (+5) | Lighter (−5) Heavier (+5) | Less sticky (−5) More sticky (+5) |

Example 4: Advantageous Skin Feels Achieved by the Polymeric Emulsifier

Three sample skin care compositions are prepared as described above, which include: (Ex. 2) 0.5% Pemulen; (Compar. Ex. 4) a common emulsifier; (Compar. Ex. 5) 0.05% Pemulen. Detailed compositional breakdown of these compositions are listed as follows (see the following table).

TABLE 7

| | Ex. 2 | Compar. Ex. 4 | Compar. Ex. 5 |
|---|---|---|---|
| Water | qs | qs | qs |
| Homosalate | 8 | 8 | 8 |
| Octocrylene | 9 | 9 | 9 |
| Butyl Methoxydibenzoylmethane | 3 | 3 | 3 |
| Phenylbenzimidazole Sulfonic Acid | 3 | 3 | 3 |
| Acrylates/C10-30 Alkyl Acrylate Crosspolymer[1] | 0.5 | 0.05 | — |
| Emulsifier[2] | — | — | X |
| NaOH | 0.66 | 0.66 | 0.66 |
| Dimethicone (5 cSt)[3] | 5 | 5 | 5 |
| Polymethylsilsesquioxane[4] | 5 | 5 | 5 |
| Disodium EDTA | 0.1 | 0.1 | 0.1 |
| 1,2-Hexanediol and 1,2-Octanediol | 0.800 | 0.800 | 0.800 |
| Phenoxyethanol | 0.375 | 0.375 | 0.375 |

[1]Pemulen TR II available from Lubrizol.
[2]Emulsifier:
[3]Xiameter ® PMX-200 silicone fluid 5cs from Dow Corning
[4]Tospearl CF600 from Momentive Rheology and Tack Test The dynamic viscosity of each composition was determined according to the Rheology Method described in Test 2 hereinabove, and the Mean Break Time values were determined according to the Tack Method described in Test 1 hereinabove. The Mean Break Time values and dynamic viscosity values are shown in the table as below. The data shows that the present compositions provide a surprisingly better balance between stickiness/stringiness (indicated by Mean Break Time) and spreadability (indicated by dynamic viscosity) by using pemulen as the emulsifier.

Panel Test

Similarly as above, the products were blinded and placed among 10 trained panelists, who were using the products at randomized sequences to give objective quantitative assessment of the product. The panelists scored the sensory feels on a −5 to +5 scale, in which stickiness, oil amount, shining are considered as negative feels, and spreadability and water-like feel are desirable feels. Each of them used these compositions on their face and rate the product at different timepoints. The results prove that the present compositions provide an advantageous skin feels by using Pemulen as the emulsifier.

Example 5: Advantageous Skin Feels Achieved by the Preferred Concentration of PBSA Three sample skin care compositions are prepared as described above, which include: (Ex. 2) 3% PBSA; (Compar. Ex. 6) 0% PBSA; (Compar. Ex. 7) 1% PBSA. Detailed compositional breakdown of these compositions are listed as follows (see the following table).

TABLE 8

| | Ex. 2 | Compar. Ex. 6 | Compar. Ex. 7 |
|---|---|---|---|
| Water | qs | qs | qs |
| Homosalate | 8 | 8 | 8 |
| Octocrylene | 9 | 9 | 9 |
| Butyl Methoxydibenzoylmethane | 3 | 3 | 3 |
| Phenylbenzimidazole Sulfonic Acid | 3 | — | 1 |
| Acrylates/C10-30 Alkyl Acrylate Crosspolymer[1] | 0.5 | 0.5 | 0.5 |
| NaOH | 0.66 | 0.66 | 0.66 |
| Dimethicone (5 cSt)[2] | 5 | 5 | 5 |
| Polymethylsilsesquioxane[3] | 5 | 5 | 5 |
| Disodium EDTA | 0.1 | 0.1 | 0.1 |
| 1,2-Hexanediol and 1,2-Octanediol | 0.800 | 0.800 | 0.800 |
| Phenoxyethanol | 0.375 | 0.375 | 0.375 |

[1]Pemulen TR II available from Lubrizol.
[2]Xiameter ® PMX-200 silicone fluid 5cs from Dow Corning
[3]Tospearl CF600 from Momentive Rheology and Tack Test The dynamic viscosity of each composition was determined according to the Rheology Method described in Test 2 hereinabove, and the Mean Break Time values were determined according to the Tack Method described in Test 1 hereinabove. The Mean Break Time values and dynamic viscosity values are shown in the table as below. The data shows that the present compositions provide a good balance between stickiness/stringiness (indicated by Mean Break Time) and spreadability (indicated by dynamic viscosity) by using a preferred concentration of PBSA.

Panel Test

Similarly as above, the products were blinded and placed among 10 trained panelists, who were using the products at randomized sequences to give objective quantitative assessment of the product. The panelists scored the sensory feels on a −5 to +5 scale, in which stickiness, oil amount, shining are considered as negative feels, and spreadability and water-like feel are desirable feels. Each of them used these compositions on their face and rate the product at different timepoints. The results prove that the present compositions provide an advantageous skin feels by using a preferred concentration of PBSA.

Example 6: Advantageous Skin Feels Achieved by the Low-Viscosity Dimethicone Compared to High-Viscosity Dimethicone Two sample skin care compositions are prepared as described above, which include: (Ex. 2) 5% low-viscosity;

(Compar. Ex. 8) 5% high-viscosity dimethicone. Detailed compositional breakdown of these compositions are listed as follows (see the following table).

TABLE 9

|  | Ex. 2 | Compar. Ex. 8 |
|---|---|---|
| Water | qs | qs |
| Homosalate | 8 | 8 |
| Octocrylene | 9 | 9 |
| Butyl Methoxydibenzoylmethane | 3 | 3 |
| Phenylbenzimidazole Sulfonic Acid | 3 | 3 |
| Acrylates/C10-30 Alkyl Acrylate Crosspolymer[1] | 0.5 | 0.5 |
| NaOH | 0.66 | 0.66 |
| Dimethicone (5 cSt)[2] | 5 | — |
| Dimethicone (high viscosity)[3] | — | 5 |
| Polymethylsilsesquioxane[4] | 5 | 5 |
| Disodium EDTA | 0.1 | 0.1 |
| 1,2-Hexanediol and 1,2-Octanediol | 0.800 | 0.800 |
| Phenoxyethanol | 0.375 | 0.375 |

[1]Pemulen TR II available from Lubrizol.
[2]Xiameter® PMX-200 silicone fluid 5cs from Dow Corning
[3]Xiameter® from Dow Corning
[4]Tospearl CF600 from Momentive Rheology and Tack Test The dynamic viscosity of each composition was determined according to the Rheology Method described in Test 2 hereinabove, and the Mean Break Time values were determined according to the Tack Method described in Test 1 hereinabove. The Mean Break Time values and dynamic viscosity values are shown in the table as below. The data shows that the present compositions provide a surprisingly better balance between stickiness/stringiness (indicated by Mean Break Time) and spreadability (indicated by dynamic viscosity) by using low-viscosity dimethicone compared to high-viscosity dimethicone.

Panel Test

Similarly as above, the products were blinded and placed among 10 trained panelists, who were using the products at randomized sequences to give objective quantitative assessment of the product. The panelists scored the sensory feels on a −5 to +5 scale, in which stickiness, oil amount, shining are considered as negative feels, and spreadability and water-like feel are desirable feels. Each of them used these compositions on their face and rate the product at different timepoints. The results prove that the present compositions provide surprisingly better skin feels by using low-viscosity dimethicone compared to high-viscosity dimethicone.

Example 7: Advantageous Skin Feels Achieved by the Absence of Fatty Alcohol

Two sample skin care compositions are prepared as described above, which include: (Ex. 2) no fatty alcohol; (Compar. Ex. 9) 1.1% fatty alcohol. Detailed compositional breakdown of these compositions are listed as follows (see the following table).

TABLE 10

|  | Ex. 2 | Compar. Ex. 9 |
|---|---|---|
| Water | qs | qs |
| Homosalate | 8 | 8 |
| Octocrylene | 9 | 9 |
| Butyl Methoxydibenzoylmethane | 3 | 3 |
| Phenylbenzimidazole Sulfonic Acid | 3 | 3 |
| Acrylates/C10-30 Alkyl Acrylate Crosspolymer[1] | 0.5 | 0.5 |
| NaOH | 0.66 | 0.66 |
| Dimethicone (5 cSt)[2] | 5 | 5 |
| Polymethylsilsesquioxane[3] | 5 | 5 |
| Fatty Alcohol | — | 1.1 |
| Disodium EDTA | 0.1 | 0.1 |
| 1,2-Hexanediol and 1,2-Octanediol | 0.800 | 0.800 |
| Phenoxyethanol | 0.375 | 0.375 |

[1]Pemulen TR II available from Lubrizol.
[2]Xiameter® PMX-200 silicone fluid 5cs from Dow Corning
[3]Tospearl CF600 from Momentive Rheology and Tack Test The dynamic viscosity of each composition was determined according to the Rheology Method described in Test 2 hereinabove, and the Mean Break Time values were determined according to the Tack Method described in Test 1 hereinabove. The Mean Break Time values and dynamic viscosity values are shown in the table as below. The data shows that the present compositions provide a surprisingly better balance between stickiness/stringiness (indicated by Mean Break Time) and spreadability (indicated by dynamic viscosity) by excluding the use of fatty alcohol.

Panel Test

Similarly as above, the products were blinded and placed among 10 trained panelists, who were using the products at randomized sequences to give objective quantitative assessment of the product. The panelists scored the sensory feels on a −5 to +5 scale, in which stickiness, oil amount, shining are considered as negative feels, and spreadability and water-like feel are desirable feels. Each of them used these compositions on their face and rate the product at different timepoints. The results prove that the present compositions provide more advantageous skin feels by excluding the use of any fatty alcohols.

Example 8: Exemplary Skin Care Compositions

The following are examples of sunscreen compositions that utilize combinations of UV-blocking actives and other ingredients including dimethicone and particulate materials (see the following table). The composition Ex. 5 to 12 are prepared similarly as in Example 1.

TABLE 11

| | Ex. 5 | Ex. 6 | Ex. 7 | Ex. 8 | Ex. 9 | Ex. 10 | Ex. 11 | Ex. 12 |
|---|---|---|---|---|---|---|---|---|
| | | | | % by weight | | | | |
| Water | Qs | qs | qs | qs | qs | qs | qs | qs |
| Diethylamino Hydroxybenzoyl Hexyl Benzoate | — | — | — | — | — | — | — | 4 |
| Bemotrizinol | — | — | — | — | — | — | — | 2 |
| Ethylhexyl Methoxycinnamate | — | — | — | — | — | — | — | 7.5 |
| Homosalate | 8 | 8 | 8 | 8 | 8 | 8 | 8 | — |
| Octocrylene | 9 | 9 | 9 | 9 | 9 | 9 | 9 | — |
| Butyl Methoxydibenzoyl methane | 3 | 3 | 3 | 3 | 3 | 3 | 3 | — |
| Phenylbenzimidazole Sulfonic Acid | 3 | 3 | 3 | 3 | 3 | 3 | 3 | 3 |
| Acrylates/C10-30 Alkyl Acrylate Crosspolymer [1] | 0.4 | 0.5 | — | — | — | — | 0.6 | 0.5 |
| Acrylates/C10-30 Alkyl Acrylate Crosspolymer [2] | — | — | 0.8 | — | 0.5 | — | — | — |
| Acrylates/C10-30 Alkyl Acrylate Crosspolymer [3] | — | — | — | 1 | — | 0.5 | — | — |
| Acrylates/C10-30 Alkyl Acrylate Crosspolymer [4] | — | — | — | — | 0.2 | 0.3 | — | — |
| NaOH | | 0.66 | 0.69 | 0.71 | 1.65 | | | 0.66 |
| Amino Methyl Propanol | 1.20 | — | — | — | — | 1.7 | 1.5 | — |
| Dimethicone (5 cSt) [5] | 5 | — | — | — | — | 5 | — | 5 |
| Cyclopentasiloxane [6] | — | 5 | — | 5 | — | — | 5 | — |
| Dimethicone (50 cSt) [7] | — | — | 5 | — | 5 | — | — | — |
| Polymethylsilsesquioxane [8] | 5 | 5 | — | 5 | — | 5 | 5 | 5 |
| Tapioca Starch (and) Polymethylsilsesquioxane [9] | — | — | 5 | — | 5 | — | — | — |
| Disodium EDTA | 0.1 | 0.1 | 0.1 | 0.1 | 0.1 | 0.1 | 0.1 | 0.1 |
| 1,2-Hexanediol and 1,2-Octanediol | 0.8 | 0.8 | 0.8 | 0.8 | 0.8 | 0.8 | 0.8 | 0.8 |
| Phenoxyethanol | 0.375 | 0.375 | 0.375 | 0.375 | 0.375 | 0.375 | 0.375 | 0.375 |

[1] Pemulen TR II available from Lubrizol.
[2] Pemulen TR I available from Lubrizol
[3] Pemulen EZ4U available from Lubrizol
[4] Carbopol ® Ultrez 20 available from Lubrizol
[5] Xiameter ® PMX-200 silicone fluid 5 cs from Dow Corning
[6] Xiameter ® PMX-0245 from Dow Corning
[7] Xiameter ® PMX-200 silicone fluid 50 cs from Dow Corning
[8] Tospearl CF600 from Momentive
[9] Dry Flo TS from AkzoNobel The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition in the form of a stable emulsion, comprising:
 a) about 7% to about 90%, by weight of the composition, of one or more Ultra-Violet (UV) blocking actives;
 b) about 2% to about 90%, by weight of the composition, of a dimethicone having a kinematic viscosity of about 0.1 cSt to about 2000 cSt as measured by the Rheology Method; and
 c) about 3% to about 90%, by weight of the composition, of a particulate material, wherein said one or more UV-blocking actives comprise a water-soluble UV-blocking active, wherein the composition exhibits a Mean Break Time of between 0.01 s and 0.7 s, as measured by the Tack Method, and a dynamic viscosity at 100s$^{-1}$ of between 0.01 PaS and 0.70 PaS, as measured by the Rheology Method; and d) wherein the composition is free of cetyl alcohol, stearyl alcohol, cetearyl alcohol, and behenyl alcohol.

2. The skin care composition according to claim 1, wherein the composition comprises about 10% to about 60%, by weight of the composition, of said one or more UV-blocking actives.

3. The skin care composition according to claim 1, wherein said water-soluble UV-blocking active is selected from the group consisting of phenylbenzimidazole sulfonic acid, terephthalylidene dicamphor sulfonic acid, disodium phenyl dibenzimidazole tetrasulfonate and combinations thereof.

4. The skin care composition according to claim 3, wherein said water-soluble UV-blocking active is phenylbenzimidazole sulfonic acid.

5. The skin care composition according to claim 1, wherein the composition comprises about 0.01% to about 50% of a water-soluble UV-blocking active.

6. The skin care composition according to claim 1, wherein said one or more UV-blocking actives is selected from the group consisting of homosalate, octocrylene, butyl methoxydibenzoylmethane, diethylamino hydroxybenzoyl hexyl benzoate, bis-ethyl-hexyloxyphenol methoxyphenyl triazine, ethylhexyl methoxycinnamate and any combinations thereof.

7. The skin care composition according to claim 1, wherein the composition comprises about 3% to about 40% of said dimethicone, wherein the kinematic viscosity of said dimethicone is about 0.5 cSt to about 1000 cSt, as measured by the Rheology Method.

8. The skin care composition according to claim 1, wherein the composition comprises about 3.5% to about 40%, by weight of the composition, of said particulate material.

9. The skin care composition of claim 8, wherein said particulate material is selected from the group consisting of sugar derivatives, silica, silicates, carbonates, silicones and mixtures thereof.

10. The skin care composition of claim 9, wherein said sugar derivatives are selected from the group consisting of aluminum starch octenylsuccinate, distarch phosphate, tapioca starch, acetyl substituted starch, adipic acid substituted starch, hydroxypropylated starch, corn starch, 2-hydropropylether modified starch, hydroxypropyl starch phosphate ester, cyclodextrins and derivatives thereof, polymethylsilsesquioxane-coated starch, and combinations thereof.

11. The skin care composition of claim 9, wherein said silicates are selected from the group consisting of talc, kaolin and a combination thereof.

12. The skin care composition of claim 9, wherein said carbonates are selected from the group consisting of magnesium carbonate, calcium carbonate and a combination thereof.

13. The skin care composition according to claim 1, further comprising dimethicone, wherein a weight ratio of dimethicone to particulate material is between 1:2 and 2:1.

14. The skin care composition according to claim 1, wherein the composition further comprises about 0.01% to about 40%, by weight of the composition, of an emulsifier.

15. The skin care composition according to claim 1, wherein the composition further comprises about 0.01% to about 5%, by weight of the composition, of a pH adjuster selected from the group consisting of potassium hydroxide, sodium hydroxide, ammonium hydroxide, aminomethyl propanol, triethanolamine, tetrahydroxypropyl ethylene diamine and combinations thereof.

16. The skin care composition according to claim 1, wherein the composition comprises:

a) 20% to 45%, by weight of the composition, of one or more UV-blocking actives that comprise phenylbenzimidazole sulfonic acid, homosalate, octocrylene, and butyl methoxydibenzoylmethane, in which the concentration of phenylbenzimidazole sulfonic acid is 2% to 5% by weight of the composition, the concentration of homosalate is 6% to 10% by weight of the composition, the concentration of octocrylene is 7% to 11% by weight of the composition, and the concentration of butyl methoxydibenzoylmethane is 1% to 5% by weight of the composition;

b) 4.5% to 6%, by weight of the composition, of a dimethicone having a kinematic viscosity of 3.5 cSt to 20 cSt as measured by the Rheology Method;

c) 4.5% to 6%, by weight of the composition, of polymethylsilsesquioxane-coated starch or polymethylsilsesquioxane;

d) 0.3% to 0.8%, by weight of the composition, of an acrylates/C10-30 alkyl acrylate crosspolymer; and e) 0.5% to 0.8%, by weight of the composition, of sodium hydroxide, wherein a ratio of acrylates/C10-30 alkyl acrylate crosspolymer to sodium hydroxide is between about 1:5 and 2:1 and wherein the composition exhibits a Mean Break Time of between 0.01 s and 0.7 s, as measured by the Tack Method, and a dynamic viscosity at 100s$^{-1}$ of between 0.01 Pa·S and 0.70 Pa·S, as measured by the Rheology Method.

17. The skin care composition of claim 16, wherein the phenylbenzimidazole sulfonic acid is present at about 3%.

18. The skin care composition of claim 1, wherein the wherein the composition exhibits a Mean Break Time of between 0.05 s and 0.4 s.

* * * * *